United States Patent
Bissmann et al.

(10) Patent No.: US 8,740,889 B2
(45) Date of Patent: Jun. 3, 2014

(54) OPHTHALMOLOGICAL LASER SYSTEM AND OPERATING METHOD

(75) Inventors: Wilfried Bissmann, Jena (DE); Hartmut Vogelsang, Jena (DE); Gregor Stobrawa, Jena (DE); Andreas Bartels, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 156 days.

(21) Appl. No.: 13/139,994

(22) PCT Filed: Dec. 16, 2009

(86) PCT No.: PCT/EP2009/067354
§ 371 (c)(1), (2), (4) Date: Jun. 15, 2011

(87) PCT Pub. No.: WO2010/070020
PCT Pub. Date: Jun. 24, 2010

(65) Prior Publication Data
US 2011/0251601 A1 Oct. 13, 2011

(30) Foreign Application Priority Data
Dec. 17, 2008 (DE) .......................... 10 2008 062 658

(51) Int. Cl.
*A61F 9/01* (2006.01)
(52) U.S. Cl.
USPC .................................. 606/5; 606/4; 128/898
(58) Field of Classification Search
USPC .................... 606/4–6, 10, 166, 170; 128/898
See application file for complete search history.

(56) References Cited

U.S. PATENT DOCUMENTS

| | | | |
|---|---|---|---|
| 5,822,035 A * | 10/1998 | Bille | 351/215 |
| 6,585,723 B1 | 7/2003 | Sumiya | |
| 2003/0073983 A1* | 4/2003 | Bille | 606/5 |
| 2003/0189689 A1 | 10/2003 | Rathjen | |
| 2006/0106371 A1* | 5/2006 | Muhlhoff et al. | 606/5 |
| 2006/0155265 A1 | 7/2006 | Juhasz et al. | |
| 2007/0179478 A1 | 8/2007 | Dobschal et al. | |
| 2008/0078752 A1 | 4/2008 | Bischoff et al. | |
| 2008/0243109 A1 | 10/2008 | Muhlhoff et al. | |
| 2008/0319464 A1 | 12/2008 | Bischoff et al. | |
| 2009/0168017 A1* | 7/2009 | O'Hara et al. | 351/205 |

FOREIGN PATENT DOCUMENTS

| | | | |
|---|---|---|---|
| DE | 102 07 535 A1 | | 9/2003 |
| DE | 10207535 A1 | * | 9/2003 |
| DE | 103 23 422 A1 | | 4/2004 |
| DE | 103 34 109 A1 | | 2/2005 |
| DE | 10 2004 009 212 A1 | | 9/2005 |
| DE | 10 2007 019 814 A1 | | 10/2008 |
| EP | 0 910 984 A1 | | 4/1999 |
| EP | 0 983 757 A2 | | 3/2000 |
| EP | 1 702 595 A1 | | 9/2006 |
| WO | WO 03/070090 A2 | | 8/2003 |

(Continued)

*Primary Examiner* — Bill Thomson
*Assistant Examiner* — Boniface N Nganga
(74) *Attorney, Agent, or Firm* — Patterson Thuente Pedersen, P.A.

(57) ABSTRACT

An ophthalmological laser system and operating method wherein laser-supported operative interventions can be achieved with higher accuracy. The cornea is irradiated with an ophthalmological laser and a detection light confocally recorded, the cornea being scanned in three-dimensions by irradiation with an illuminating laser power using a scanner unit along several directions at several points. Using the simultaneously recorded detection light the position and/or shape of a posterior boundary surface of the cornea is determined. A lamella parallel to the posterior boundary surface can then be cut.

9 Claims, 7 Drawing Sheets

(56) References Cited

FOREIGN PATENT DOCUMENTS

| WO | WO 2006/051364 A1 | 5/2006 |
| WO | WO 2007084694 A2 * | 7/2007 |
| WO | WO 2007/106326 A2 | 9/2007 |
| WO | WO 2007106326 A2 * | 9/2007 |
| WO | WO 2008/040436 A1 | 4/2008 |
| WO | WO 2008/064771 A1 | 6/2008 |
| WO | WO 2009/146906 A2 | 12/2009 |

* cited by examiner

OPHTHALMOLOGICAL LASER SYSTEM AND OPERATING METHOD

PRIORITY CLAIM

The present application is a National Phase entry of PCT Application No. PCT/EP2009/067354, filed Dec. 16, 2009, which claims priority from German Application No 102008062658.9, filed Dec. 17, 2008, the disclosures of which are hereby incorporated by reference herein in their entirety.

FIELD OF THE INVENTION

The invention relates to an ophthalmological laser system with a laser, the radiation of which is focusable in an examination region via an illumination beam path, which exhibits a scanner unit; particularly with an immobilization device for an eye positioned in the examination region. Furthermore, the invention relates to an operating method for an ophthalmological laser system.

BACKGROUND

In ophthalmology it has been established, in case of defective vision, to form the cornea of the human eye with its approximate thickness of 500 μm through ablation of tissue in order to correct myopia, hypermetropia, and astigmatism. This is called refractive surgery. In addition, the transplant of pieces of the cornea from a donor eye into a recipient's eye has been established in order to replace diseased or damaged corneal tissue and therefore retain or restore vision. Both methods are collectively termed keratoplasty and can be executed by means of lasers. In the so-called lamellar keratoplasty, a single disc from a donor cornea is transplanted in or onto a recipient's cornea.

Anatomically, the human cornea consists of five different tissue layers. From anterior to posterior they are: Epithelium, Bowman's membrane, stroma, Descemet's membrane, and endothelium. Thereby, the stroma takes up the largest volume.

During laser-supported intrastromal keratomileusis (LASIK), a flap with an approximate thickness of typically 80 μm or more is detached from the cornea and folded up. For example, it is known from US 2006/0155265 A1 (Intralase Corp.) to cut the flap by means of a femtosecond laser system (Femto-LASIK). Such devices are also called laser microkeratomes. Thereby, a photodisruption is produced in the focus, which leads to a minimal formation of bubbles in the stromal tissue. If focal spot is set next to focal spot by means of a scanner system, incisions (perforations) can be made in the cornea.

The ablation of the stromal tissue, necessary for a refractive correction, is subsequently executed conservatively by means of an excimer laser. After treatment, the flap is folded back. Disadvantageously, said method requires two laser systems.

In WO 2008/064771 A1 (Carl Zeiss Meditec AG), a femtosecond laser system is described which can also prepare the flap but is additionally capable of separating the ablation of stromal tissue, necessary for a refractive correction, through multiple incisions for the preparation of a lenticle. This can be called femtosecond lenticle extraction. Subsequently, the lenticle can be removed after opening the flap, e.g., with a pair of pincers. Then the flap is folded back again. For said method, only one laser system is required, the use of an excimer laser can be forgone. Such a laser system also allows for the execution of incisions during the transplant of corneal tissue. Thereby, the femtosecond laser system can be used for incisions on the donor eye as well as for incisions in the recipient's eye.

During keratoplasty (refractive correction, transplant), the shape of the cornea of the human eye is problematic. For example, the refractive power of the cornea depends on its shape. The anterior corneal surface is in a first approximation a toric surface and is generally described through two radii of a certain axial position perpendicular to one another. The thickness of the cornea also increases towards its periphery. In addition, further irregularities of the corneal thickness can occur with certain pathologies.

According to prior art, for the planning of a laser-supported keratoplasty, the shape of the cornea is specially measured (pachymetry), e.g., contactless by means of a Scheimpflug camera or an optical coherence tomography system (OCT) for the anterior eye segment. The contacting measurement by means of ultrasound is also known. However, during the actual surgery, the cornea is held on the femtosecond laser through the application of a contact glass and suctioning of the eye, whereby, as a rule, the shape of the cornea is altered (applanation).

As a result, the parameters of the shape of the cornea, obtained outside of the actual surgery, are now, among others, only meaningful within limits. Therefore, the accuracy of the laser treatment, as far as it is based on the measured shape, is limited. As a result, the transplant can deviate from its planned shape and not be implanted optimally in the recipient's eye. This can lead to complications, e.g., the detachment of the transplant or glaucoma due to a shift of the transplant.

Regardless of the shape of the cornea, there is also the problem that in some cases optically opaque bubbles (opaque bubble layer—OBL) may appear during the perforation of corneal tissue by means of femtosecond laser radiation with lamellar incisions. This refers to an area in the immediate surroundings of the actual laser incision, whereby the forming of the laser-induced micro-gas bubbles not only occurs in the plane of the incision. Depending on position and characteristic of an OBL field, the perforation of the tissue in this area is not ideal. In comparison to the surrounding area, the result is a more difficult manual detachment of the tissue components to be separated, which leads to tissue stress and/or to a prolonged duration of surgery. Therefore, prior art attempts to avoid the formation of OBL. For example, this is accomplished through optimization of treatment parameters, such as pulse energy and spot distance and/or track distance. The modification of the incision geometry towards deeper incisions, e.g., greater flap thickness or the creation of a low-lying gas pocket, e.g., at a depth of 250 μm, can contribute to a decrease of the frequency of OBL. However, experience has shown that even under said conditions, OBL occurs in some eyes. Furthermore, modifications of the incision geometry and gas pockets are disadvantageous with regard to the preservation of as much residual stromal thickness as possible.

SUMMARY OF THE INVENTION

The invention is based on the task of improving an ophthalmological laser system and a corresponding operating method of the initially mentioned type in such a way that a laser-supported surgical procedure within the course of a keratoplasty is made possible with greater accuracy, whereby improved chances for success and a decreased treatment risk are to be achieved and/or that an easier manual detachment of perforated tissue components is made possible.

According to a first aspect of the invention, a detection beam path with a confocal aperture diaphragm and a detector for mapping of detection light from the focused part of the examination region is provided in an ophthalmological laser system. Furthermore, a control unit for irradiating the cornea by means of the laser and recording of detection light by means of the detector is provided, whereby it scans the cornea three-dimensionally through irradiating said cornea at illumination laser power by means of the scanner unit at several spots and simultaneously mapping detection light from said spots. By means of the detection light, the control unit determines position and/or form of a posterior boundary layer of the cornea. Said information can subsequently be displayed or immediately processed further and/or stored for later utilization.

The posterior boundary layer is the transition from the endothelium, the posterior border of the cornea, to the aqueous humor of the eye. At said media border, a refractive index jump and an increased reflection occur which can be measured with great accuracy with a confocal detector. Measuring devices, such as a Scheimpflug camera or an OCT system are not required thereto. For example, the detection beam path can be part of a confocal laser scanning microscope (LSM) which is provided in addition to the treatment laser.

Through the measuring of the posterior boundary layer, said layer can, advantageously, be used as a reference plane for keratoplastic incisions.

Particularly with an immobilization device with a contact glass, whose boundary layer on the side facing the eye exhibits a radius of curvature which differs from the eye, the positional change/deformation of the cornea, resulting from the applanation, and particularly its posterior boundary layer, is taken into consideration during the measurement.

Through the knowledge of the form and/or position of the posterior boundary layer and information about form and/or position of the anterior boundary layer presupposedly known or to be measured, the actual shape of the cornea is known with great accuracy for a subsequent laser surgical treatment. This also applies particularly for the shape in applanated condition insofar as an appropriate contact glass is used. This way, a thickness distribution of the cornea in terms of a pachymetric mapping (pachy-map) can be determined and utilized in the irradiation planning. Particularly, the anterior and posterior radii of the cornea can be determined, which are relevant for the determination of the refractive index ratios. With conventional methods, it was possible to obtain said parameters only outside of the actual keratoplastic surgery. A possible applanation could not be taken into account. However, the invention not only allows for a more accurate determination of the geometric parameters for surgery but also for the measurement during or at least immediately before surgery in the treatment condition of the patient. As a result, inaccuracies which result from undocking and redocking of the eye, are avoided. Due to the now possible, highly accurate reference to the posterior boundary layer, a keratoplasty can be performed with great accuracy, resulting in improved chances for success and a decreased treatment risk.

The posterior boundary layer can be, e.g., analytically depicted through adaptation of a model function, particularly with Zernike polynomials, by means of an adjustment calculation at the measuring points. Since it is a curved surface, the detection light must be mapped from at least four points of the posterior boundary layer. With a low number of sampling points, additional facts about the deformation of the cornea under applanation are required a priori for an analytical depiction. Such requirement is not applicable with a large number of sampling points.

In order to determine the position and/or form of the anterior boundary layer, the principle for measuring the boundary layer of the contact glass which faces the eye, as described, e.g., in WO 2008/040436 A1, can be applied. The measurement of the anterior boundary layer can be performed before or after the measurement of the posterior boundary layer, but preferably in a narrow temporal connection with said measurement, particularly during or immediately before a keratoplastic surgery.

Advantageously, the control unit, after determining form and/or position of the posterior boundary layer of the cornea, can determine irradiation control data for a laser surgical treatment, while taking into consideration the determined position and/or form of the posterior boundary layer, and irradiate the cornea by means of the laser at surgical therapy laser power in accordance with the determined irradiation control data. As a result, a keratoplasty with great accuracy is possible since the actual current position of the posterior boundary layer allows for the highly accurate placement of incisions relative to said boundary. Since the measurement of the posterior boundary layer can be performed during the treatment condition of the patient, the likelihood of a substantial change of position and/or form is slim.

In an example embodiment, the control unit is designed in such a way that it can cut a lamella parallel to the posterior boundary layer, i.e., parallel to the endothelium, based on the determined position and/or form of the posterior boundary layer. Particularly, the lamella can be cut exclusively from the endothelium. Of course, it is also possible to cut a lamella from the endothelium and the stroma. In order to cut an anterior or posterior lamella parallel to the cornea surface in the back, the radii of the boundary layers in the back are, according to the invention, determined beforehand. With the laser system and the operating method, according to the invention, said parameters can be determined with great accuracy and in the quasi-absolute coordinate system of the laser. Therefore, the invention allows particularly for endothelial keratoplasty with great accuracy and little effort.

Expediently, an immobilization device for the cornea and/or the eye is provided, whereby the control unit immobilizes the cornea and/or the eye through activation of the immobilization device prior to the (first) detection cycle. This can lead to the applanation of the cornea if a contact glass is used. The control unit releases the immobilization after termination of the irradiation. Due to the immobilization, a change in position or form of the cornea between detection/determination of the posterior boundary layer and treatment is avoided. In future embodiments without immobilization of the eye, or at least the cornea, the movement of the cornea and/or the entire eye can be traced contactless with optical means in order to immediately determine a change in position of the cornea and adjust the beam guidance accordingly. However, even with such embodiments, the posterior boundary layer must first be measured in order to achieve great accuracy of a keratoplasty.

A measurement of the posterior radii, once suctioned intraoperatively directly before the laser incision with the femtosecond laser, gathers the required parameters for the definition of the individual front and back surface of the retina through the contact glass on the eye, also particularly in cases where the eye is applanated. This allows for the cutting of a thin lamella in predetermined form relative (e.g., parallel) to the posterior surface of the cornea within the course of a lamellar keratoplasty with great accuracy.

The invention is also suited for the measurement of the thickness distribution of the cornea in other keratoplastic procedures. Such a procedure is known, e.g., from WO 2006/

051364 A1 (20/10 Perfect Vision Optische Geraete GmbH). In said procedure, incisions in the stromal tissue are made with a femtosecond laser in order to create a coherent cavity, particularly with a cylindrical shape, without ablation of tissue. When the cavity collapses due to the intraocular pressure, the cornea relaxes and takes on a new form with altered curvature. This way, defective vision is to be improved. The certainty of said procedure can be improved, according to the invention, whereby at first the thickness distribution of the cornea is determined and, based on said determination, safety distances from the adjacent membranes are monitored.

Said measurement can be performed particularly intraoperatively without temporary undocking of the eye.

Advantageously, a beam splitter for decoupling of the detection beam path is arranged in the illumination beam path. This way, the illumination beam path and the detection beam path can be aligned to one another with great accuracy. As a result, the same optical elements (focusing optics, etc.) can be utilized twice. Thereby, embodiments are preferred which, in addition to the illumination laser power, can be adjusted to a surgical therapy laser power. As a result, the same laser can be utilized for the illumination during the determination of form and/or position of the posterior boundary layer of the cornea as well as for the subsequent treatment with great positioning accuracy. Thereby, the use of the same laser for measurement and treatment allows for great accuracy for the positioning of the treatment focus since the measurement of the posterior boundary layer can be performed in the quasi-absolute reference system of the treatment laser.

In an advantageous embodiment, the beam splitter is a polarization beam splitter, which decouples the detection light on the detector in such a way that it exhibits a polarization direction different from the emitted illumination light. A large portion of the light, which impinges on the beam splitter from the examination region, originates from reflections on the optical components of the beam path, e.g., the surfaces of the focusing optics; therefore, it exhibits the same polarization direction as the illumination light. Since the beam splitter only directs light as detection light to the detector with a different polarization direction, such stray light is suppressed. However, light backscattered in the cornea exhibits an altered polarization direction. Therefore, the detection of the light backscattered in the cornea is possible with greater accuracy.

Moreover, due to the polarization properties of the cornea, varying polarization properties of the introduced diagnostic radiation are advantageous for the image generation within varying areas of the cornea.

Said properties can be produced through one or several polarizing optical elements in the illumination beam path.

Advantageously, a polarization filter is positioned in the detection beam path between the beam splitter and the detector, which is fixed in terms of rotation or rotatable with regard to its polarization direction. With regard to its effect, a polarization filter, which is fixed in terms of rotation, corresponds to the aforementioned polarization beam splitter. Due to the polarization properties of the cornea, a selection of the polarization direction backscattered to the confocal detector through a twist of the polarization filter assigned to the detector is advantageous for the efficient diagnosis of particular areas of the cornea. Hence, a complete detection of an overall image with high contrast is accomplished through multiple scanning at various settings of the polarization filter to a respective individual image and appropriate superimposition of the individual images to the overall image. Instead of a separate polarization filter, a polarization beam splitter can also be designed rotatable in order to selectively detect stray light of varying polarization directions. However, the determination of position and/or form of the posterior boundary layer is also possible with a polarization filter/polarization beam splitter, which is fixed in terms of rotation, or entirely without polarization filtering, particularly by means of a single scan cycle. A single scan cycle can be executed in a short period of time.

It is possible to achieve an even greater signal strength, whereby an optical phase retardation system in the illumination beam path between the focusing optics and the examination region is arranged in such a way that the passing illumination light obtains a polarization direction corresponding to the decoupled detection light. As a result, the stray light exhibits the same polarization direction as the radiation from the laser, while the illumination light, which reaches the cornea and is modified in the phase retardation system, obtains a defined, different polarization direction. Through the selection of the light of said polarization direction as detection light by means of the polarization beam splitter, only such light, which was backscattered in the cornea, is detected almost exclusively. Stray light, which originates from reflections on optical components, is even more effectively kept away from the detector.

In order to improve the image contrast, a lock-in amplifier, coupled with the laser, can be provided for the detector. This allows for the mapping of the detector light with great sensitivity so that a possible treatment can be executed with great accuracy.

For the three-dimensional scanning of the cornea, the radiation exposure can be reduced in such a way that two consecutive scan points differ from each other in all three spatial coordinates. Through this type of scanning, representative data about form and/or position of the posterior boundary layer of the cornea can be obtained in a short period of time. Alternatively, during scanning for either one or several series of scan points respectively, it is possible to maintain one or two spatial coordinates constant and to only vary the two coordinates and/or the one remaining spatial coordinate. As a result, several series of scan points can be illuminated and detected in a plane curve at a constant z-coordinate, respectively. Alternatively, one series of scan points can be mapped with a constant x- and y-coordinate while varying the z-coordinate, e.g., beginning at the contact glass. For the latter approach, the curve in z-direction must inevitably pierce through the posterior boundary layer. Once this has been identified through a significant increase of the intensity of the detection light, the z-scan can be terminated at said x/y coordinates and restarted at a different x/y point.

Preferred are embodiments, in which one or two mirrors of the scanner unit oscillate during scanning, particularly, oscillate harmonically. A control of the scanners in the form of harmonic oscillations, such as sine functions, is technically particularly advantageous. Controlling the x-y-scanners in such a way that one of the scanners is controlled with exactly double the frequency than that of the other scanner results in a Lissajous figure, which resembles the FIG. 8. Simultaneously to the x-y-scan, e.g., a monotone or a strictly monotone variation of the focus distance, i.e., a z-scan, takes place. This results in a continuous space curve. In the case of the above frequency ratio of 2:1, it exhibits the form of several offset figure eights, layered by depth.

This particular form and generally all frequency ratios of 2N:1 (N=1,2,3, . . . ) are advantageous since two key incisions and the optical axis are available for the determination of sampling points for the posterior boundary layer, which allows for great accuracy for the determination of form and/or position of the posterior boundary layer.

Preferably, a pulse frequency of the laser light, depending on the motion speed of a focal point of the laser beam, is set or reversed relative to the cornea. As a result, the radiation exposure of the cornea and the eye overall can be decreased during the detection of the posterior boundary layer. For example, for a slow motion speed of the focal point, which, e.g., occurs during the motion reversal of oscillating scanners, a low pulse frequency is used. For a high motion speed, a high pulse frequency is used in order to obtain a high spatial resolution.

The invention also comprises advantageous embodiments, wherein a treatment cycle is followed by a repeated detection cycle with determination of the posterior boundary layer, followed by another treatment cycle. As a result, the accuracy of the treatment can be increased, e.g., through an iterative approach to an optimal treatment outcome. Even during the first treatment, changes in form and/or position of the cornea and therefore also its posterior boundary layer can occur due to swellings. Through a remeasuring between two treatment cycles, such and other changes can be taken into consideration.

Expediently, a darkfield value is subtracted from the mapped detection light. This can either be a mutual darkfield value for all scan points or several point-specific darkfield values. This embodiment allows for a greater accuracy of the imaging of the light backscattered in the cornea.

In addition to the ophthalmological laser system and an operating method, the invention also comprises a computer program for said method as well as a control unit, which is designed for the execution of the operating method, according to the invention.

Advantageously, the step of irradiating and scanning the cornea can be executed several times along a scan curve, whereby the scan curve is utilized during each scan cycle in a varyingly offset and/or varyingly rotated position. Since a depth scan and a side scan through the confocal detection system only results in a sectional image of the cornea, an almost complete three-dimensional analysis is possible, for example, through repetition with a rotated scan curve in increments of 1°, 5°, 10°, ... 90° centrally symmetrical to the first scanning cycle.

In addition to the ophthalmological laser system and an operating method for said system, the invention in accordance with its first aspect also comprises a computer program as well as a control unit, which are designed for the execution of an operating method or keratoplasty method, according to the invention. Furthermore, it comprises a general surgical method for the execution of the keratoplasty, whereby a position and/or form of the posterior boundary layer of a cornea is determined through confocal detection, and an endothelial lamella parallel to the posterior boundary layer is cut by means of the determined position and/or form of the posterior boundary layer.

According to a second aspect of the invention, a light source for the illumination of the eye, a detector for mapping detection light from the examination region, and a control unit are provided in an ophthalmological laser system. The control unit determines irradiation control data for a laser surgical treatment, activates the immobilization device, irradiates the cornea by means of the laser at a surgical therapy laser power in accordance with the determined irradiation control data, illuminates the cornea by means of the light source, and identifies an area of the cornea in which opaque bubbles are present by means of the detection light mapped by the detector, irradiates at least the identified area of the cornea again by means of the laser at a surgical therapy laser power, and deactivates the immobilization device, whereby it leaves the immobilization device permanently activated between the first irradiation and the last repeated irradiation.

Expediently, a consent of an operator can be prompted prior to the repeated irradiation. Said aspect of the invention also comprises a general method for the execution of a keratoplasty on a cornea of an eye, whereby the eye is immobilized by an immobilization device, whereby the cornea is irradiated by a laser at a surgical therapy laser power, and whereby the immobilization is released at the end of the irradiation. After the irradiation of the cornea and prior to the release of the immobilization, an area of the cornea is identified, according to the invention, which contains opaque bubbles. Then, also prior to the release of the immobilization, at least the identified area of the cornea is irradiated again by the laser at surgical therapy laser power.

Through the identification of OBL, particularly automated by a control unit, and repeated irradiation at least in the area affected by OBL, a significantly easier and therefore improved manual detachability of tissue components is achieved in the affected area. Due to the continuous immobilization of the patient's eye, the repeated irradiation can be executed with great positioning accuracy, particularly relative to the positions in the already determined irradiation control data. The repeated irradiation with continuous immobilization can be termed as intraoperative "recutting."

Advantageously, the repeated irradiation can be performed in accordance with the determined irradiation control data or in accordance with a subset thereof, particularly through the control unit. This equals an at least partial repetition of the planned laser incision, hence no new irradiation control data have to be determined. As a result, the repeated irradiation can be executed in as short a time as possible, minimizing the risk of a change of position of the eye. Due to the continuous immobilization, initial incisions are reproducible with great accuracy.

Alternatively to the at least partial repetition of an initial incision, one or several laser incisions can be performed, the irradiation control data of which differ from the initial incision(s). Particularly, the irradiation energy, the spot and/or track distance as well as the scan direction can be varied in order to achieve a better treatment outcome.

According to the invention, the operating method for an ophthalmological laser system, the laser of which is switchable between an illumination laser power and a therapy laser power, and the laser light of which is focusable three-dimensionally variable in a cornea, can also be executed without the automatic execution of the steps "illumination," "detection," "identification of OBL," and "triggering recutting." Thereto, the following steps are provided:

Determination of irradiation control data for a laser surgical treatment;

Activation of the immobilization device;

Irradiation of the cornea by means of the laser at a surgical therapy laser power in accordance with the determined irradiation control data;

Identification of an area of the cornea, which contains opaque bubbles, by means of images of the cornea, e.g., manually through a microscope or by means of a camera and an image display;

Repeated irradiation of at least the identified area of the cornea by means of the laser at a surgical therapy laser power;

and

Deactivation of the immobilization device, whereby the immobilization device remains permanently activated between the first irradiation and the last repeated irradiation. The identification, e.g., is performed visually through an operator, and the triggering of the repeated irradiation is performed manually also by the operator.

Preferably, the irradiation control data utilized for the repeated irradiation of the cornea are stored in a treatment database. For example, the treatment database can be managed in the control unit or an external control computer. Advantageously, the stored irradiation control data can be used during later irradiation cycles for the optimization of irradiation control data.

In addition to the ophthalmological laser system and an operating method for said system, the invention in accordance with its second aspect also comprises a computer program as well as a control unit, which are designed for the execution of an operating method or keratoplasty method, according to the invention. Advantageously, they can be designed for the provision of a control element for triggering a repeated irradiation of the cornea, whereby said provision is executed prior to a deactivation of an immobilization device.

The initial determination of irradiation control data can be executed in all aspects of the invention before or after an activation of the immobilization device for the eye, particularly temporally beforehand in preparation of the actual operation.

BRIEF DESCRIPTION OF THE DRAWINGS

In the following, the invention shall be further explained by means of embodiment examples.

It is shown in.

In all drawings, all corresponding parts bear the same legend.

DETAILED DESCRIPTION

Figure 1:
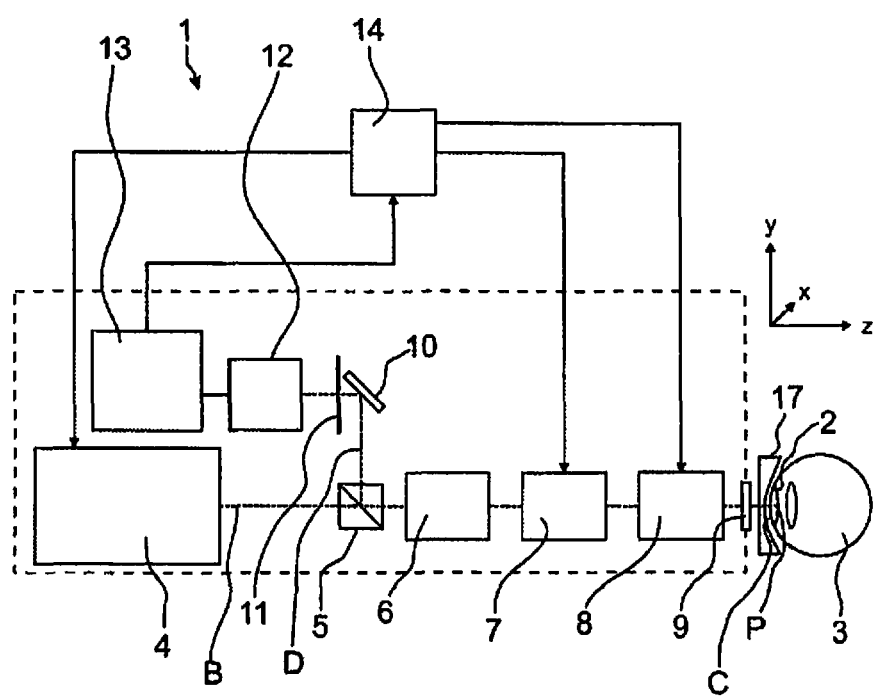
FIG. 1 is an ophthalmological laser system for the analysis of the cornea.

FIG. 1 shows an exemplary ophthalmological laser system 1 for identification and localization of the posterior boundary layer of a cornea 2 of an eye 3 with regard to form and position of the boundary layer. The laser system 1 comprises a laser 4, a polarization beam splitter 5, scan optics 6, a scanner unit 7, focusing optics 8, and an optical phase retardation system 9, which together form an illumination beam path B; as well as a deflection mirror 10, a confocal aperture diaphragm 11, and a detector 12, which form a decoupled detection beam path D. In addition, the laser system 1 comprises an amplifier 13 and a control unit 14. Between the laser system 1 and the eye 3, an immobilization device 17 with a contact glass for the eye 3 is positioned, behind which lies the examination region. On the side facing the eye 3, the contact glass can exhibit a spherical, planar, eye-curved, or any other surface rotationally symmetric around the optical axis. This example shows a spheric curvature, whereby the cornea 2 is applanated in an immobilized (e.g., suctioned) condition.

Other embodiments for the realization of the solution, according to the invention, are possible (not depicted). For example, the beam splitter 5 can be designed non-polarizing. In this case, the phase retardation system 9 can be omitted. In further embodiments (not depicted), the immobilization device 17 can immobilize the eye 3 instead of the cornea 2, whereby no contact glass is used. Hereby, the cornea 2 can be surrounded, e.g., with a liquid or an inert gas. Particularly, in such a case, the movement of the cornea 2 can be tracked with optical means in order to trace the movement with the laser beam for detection and/or treatment.

For example, the laser 4 is designed as a pulsed TiSa infrared laser with a pulse length between 100 fs and 1000 fs. It emits laser radiation at an eye-safe illumination laser power in the range of 100 mW. The scanner unit 7 comprises, for example, a number of galvanometric mirrors for the deflection of the laser radiation in the x- and y-directions via the cornea 2. The focusing of the laser radiation in z-direction along the optical axis is effected, e.g., through a movable lens or lens group within the scan optics 6 or the focusing optics 8, or alternatively through a movable tube lens (not depicted). The optical phase retardation system 9, for example, is designed as a $\lambda/4$ plate, which forms a border of the laser system 1. The detector 12, e.g., is designed as a photomultiplier (PMT) or as an avalanche photo diode (APD) since the light intensities to be mapped are low.

The amplifier 13 is designed as a lock-in amplifier and connected to the detector 12 as well as the laser 4.

The pulsed IR laser radiation emerges from the laser 4 and initially passes unchanged through the polarization beam splitter 5. Then it is focused via scan optics 6, scanner unit 7, and focusing optics 8 as illumination light on a scan point P in the cornea 2. Said scan point P can be shifted in the cornea 2 by means of the scanner unit 7 and a movable lens or lens group within the scan optics 6 or the focusing optics 8 in x-, y-, and z-direction. Thereby, the optical phase retardation system 9 effects a defined change of the polarization direction of the illumination light passing through.

At the boundary layers 2.1, 2.2 and inside the cornea 2, a scattering/reflection of the IR radiation occurs, whereby the radiation is partially depolarized. Backscattered/reflected light also impinges on the illumination beam path B and there returns all the way back to the polarization beam splitter 5. The radiation components with unchanged polarization status pass through the polarization beam splitter 5 onto the laser 4. This refers particularly to reflections which originate from the scan optics 6 or the focusing optics 8. Such radiation components, which, after passing through the phase retardation system 9 and/or through depolarization in the eye 3, exhibit a changed polarization status in the cornea 2, are deflected by the polarization beam splitter 5 as detection light into the detection beam path D to the detector 12. The detection light passes via a deflection mirror 10 through the confocal aperture diaphragm 11 onto the detector 12. In an alternative embodiment (not depicted), the deflection mirror 10 can be omitted or replaced by other beam guidance units. The confocal aperture 11 acts as discriminator in the z-direction, therefore, spatially resolved, only backscattered light is detected from a low focus volume. The control unit 14, through the deflection of the illumination light in x- and y-direction by means of the scanner unit 7 and change of the focusing in z-direction by means of the focusing optics 8, can irradiate random scan points P inside of the cornea 2 with illumination light and determine the strength of the backscatter at said points P via the intensity of the corresponding detection light.

In the depicted embodiment, the optical phase retardation system 9 between the eye 3 and focusing optics 8 effects a defined rotation of the polarization direction of the passing illumination light, while stray light, previously reflected at the optical components, maintains the original polarization direction. As a result, the relative intensity of the detection light is increased since the polarization beam splitter 5 separates only light with deviating polarization direction as detection light. In alternative embodiments (not depicted), the optical phase retardation system 9 can be omitted. Alternatively or additionally, additional polarizers (not depicted) can be positioned in the illumination and/or detection beam path in order to improve the signal quality. In another embodiment, the phase retardation system can be realized as depolarizer so that the extent of the phase retardation varies via the beam profile.

Since the signals registered at the detector 12 exhibit a very low intensity, the electronic amplifier is adjusted to an optimized signal-to-noise ratio. A particularly advantageous embodiment is the lock-in amplifier, which is temporally synchronized with the pulse generation and/or the repetition frequency of the laser 2. Other embodiments, for example, utilize so-called boxcar techniques or scanning techniques (sampling) with adding up or averaging for noise suppression. Advantageously, the entire amplifier system of the detector signal exhibits a nonlinear characteristic. However, a peak detector and/or a sample-and-hold circuit can also be used to achieve signal improvement.

In an alternative embodiment (not depicted), the detection beam path D can be arranged separate from the illumination beam path, whereby it is provided with its own objective. Hereby, a separate laser can be provided for the illumination during one or several detection cycles.

In such an embodiment, the laser 4 of the treatment system 1 can be operated, e.g., permanently at therapy laser power without an attenuator.

Figure 2A:
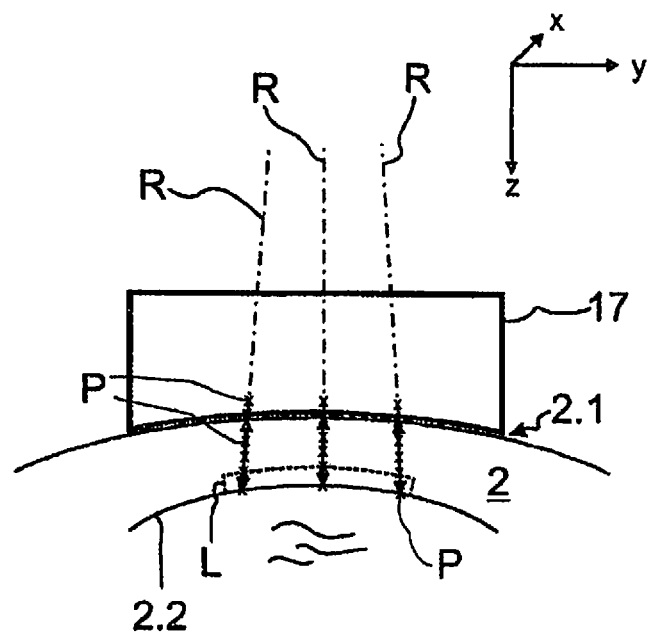
FIG. 2 depicts the measurement of the cornea up to the posterior boundary layer.
Figure 2B:
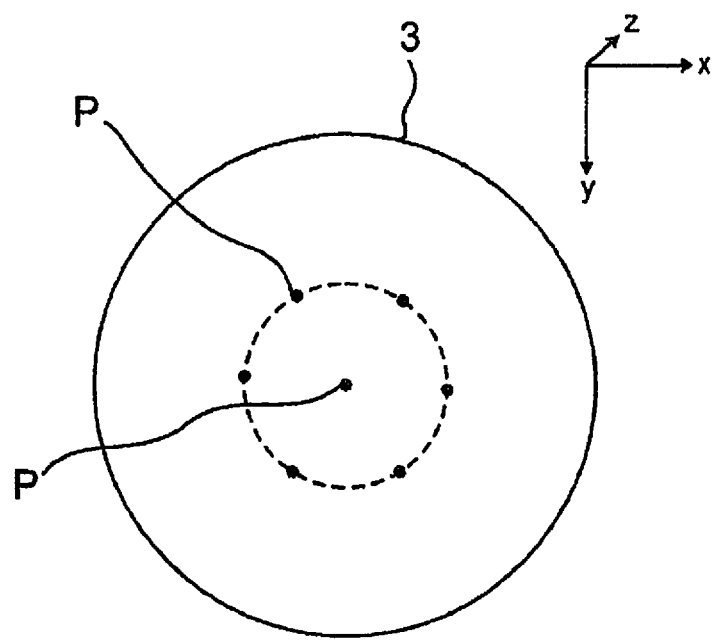

In order to determine information about form and position of the posterior boundary layers 2.2 of the cornea 2 with great accuracy in a short period of time, a suitable spatial distribution of points P is scanned confocally, regardless of the embodiment. For example, as depicted in FIG. 2, several series (for reasons of simplification, only three in partial FIG. 2A) of scan points P can be scanned along an appropriate number of different paths R with constant x- and y- coordinates. Expediently, one of the paths R lies on the optical axis of the laser system 1 and the remaining paths, e.g., in equidistant angular steps on a concentric circle around the optical axis. Partial FIG. 2B depicts the frontal view of the eye 3. Only one of the scan points P of each path series is depicted. Altogether, seven paths R are scanned along the z-direction, respectively.

For example, the scan can start along an individual path R within the contact glass 17, the measurements of which are known, or on its surface which faces the eye and continue in equidistant z-steps up to a distance of e.g., 1.5 mm from the contact glass. For the purpose of acceleration, it is also conceivable to start the scan at a distance of 100 μm to 300 μm from the surface of the contact glass 17 which faces the eye. Also, the scan cannot be executed to a fixed depth but, e.g., only until the second significant increase of the detection light intensity as characteristic for the posterior boundary layer 2.2. Four or six different paths R with an appropriate number of scan point series are expedient. From the thereby obtained values for the intensity of the backscatter, the form and position of the posterior boundary layer 2.2 can be reconstructed since the backscatter at the boundary layers (anterior, posterior) 2.1,2.2 is, in comparison with the stroma and the inner layers, intensified. For example, by means of said parameters, a thickness distribution of the cornea 2 in applanated condition can be determined. If the contact glass radius is known, it is also possible to deduce the posterior radii of curvature of the cornea 2 in applanated condition from the form and/or position of the posterior boundary layer 2.2.

For example, with such data, the irradiation pattern for the laser 4 can be computed for the calculation of an endothelial lamella L parallel to the posterior boundary layer 2.2. As a result, the invention allows for an endothelial keratoplasty with great accuracy. If only a few sampling points were determined, accuracy can be improved through the utilization of known mathematical models for the calculation of the deformation of an applanated cornea.

The positioning accuracy of the positions of the measurements is relatively noncritical since the thickness changes of the cornea in the area to be measured are usually smaller than 100 μm. A positioning accuracy (x-y) of +/−100 μm is sufficient. The accuracy of the thickness measurement is more important. An accuracy of +/−5 μm is expedient.

Figure 3A:
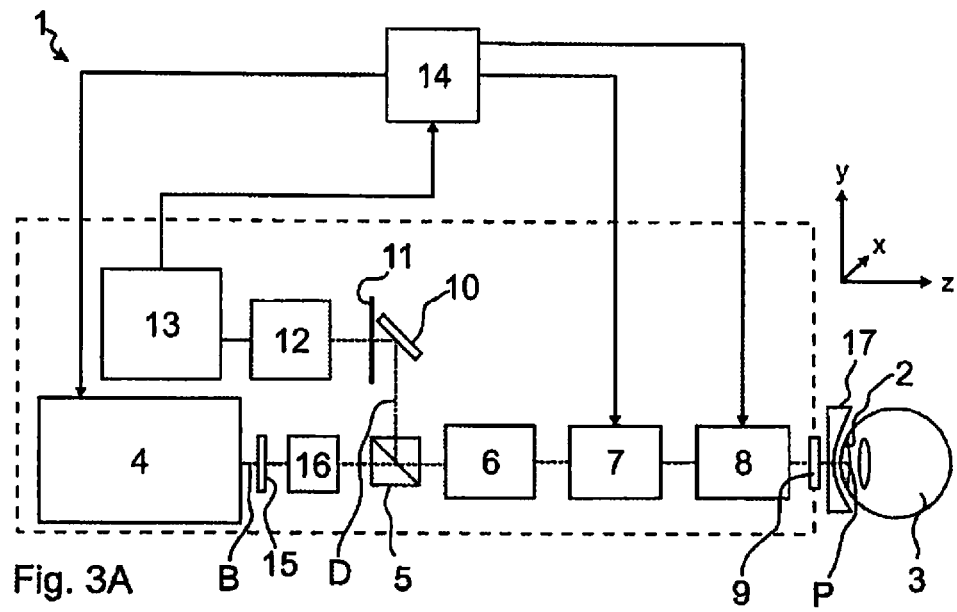
FIG. 3 is an ophthalmological laser system for the analysis and treatment of the cornea.
Figure 3B:
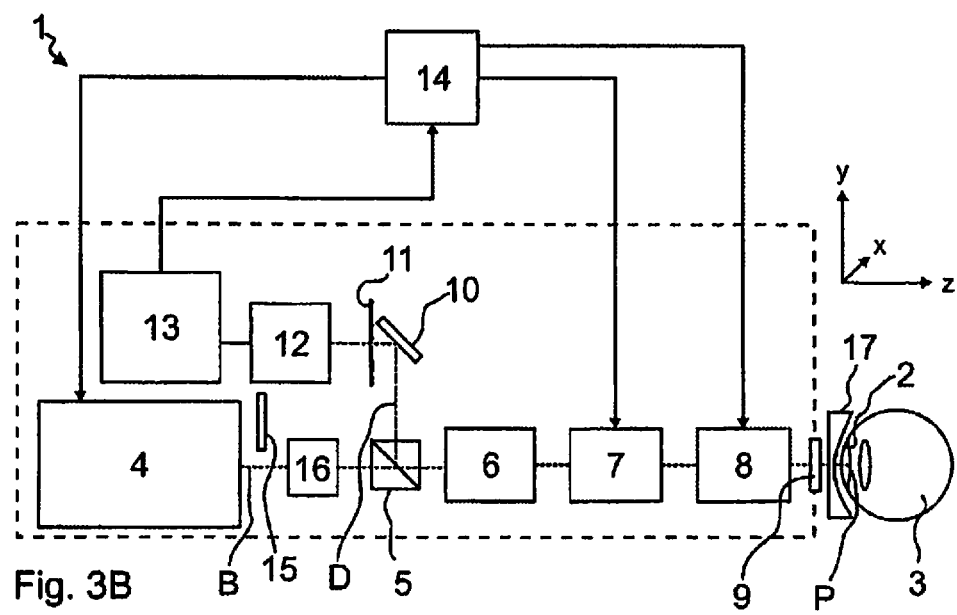

FIG. 3 shows an exemplary ophthalmological laser system 1 for the highly accurate execution of a keratoplasty. It corresponds to a large extent to the laser system 1 in accordance with FIG. 1 but is additionally equipped with an attenuator 15, which can be tilted into the illumination beam path B, and a modulator 16, e.g., an acousto-optical modulator. The attenuator 15 is used for switching between an illumination laser power and therapy laser power. Illumination laser power is obtained through the attenuator 15, tilted into the illumination beam path B, and therapy laser power is obtained without the attenuator 15. The optical components, particularly optics 6 and 8, are optimized, corrected, and synchronized towards the goal of a best possible focus miniaturization. For example, its optical aberrations are minimized to a high degree, requiring only a low energy input for a photodisruption.

Figure 4:
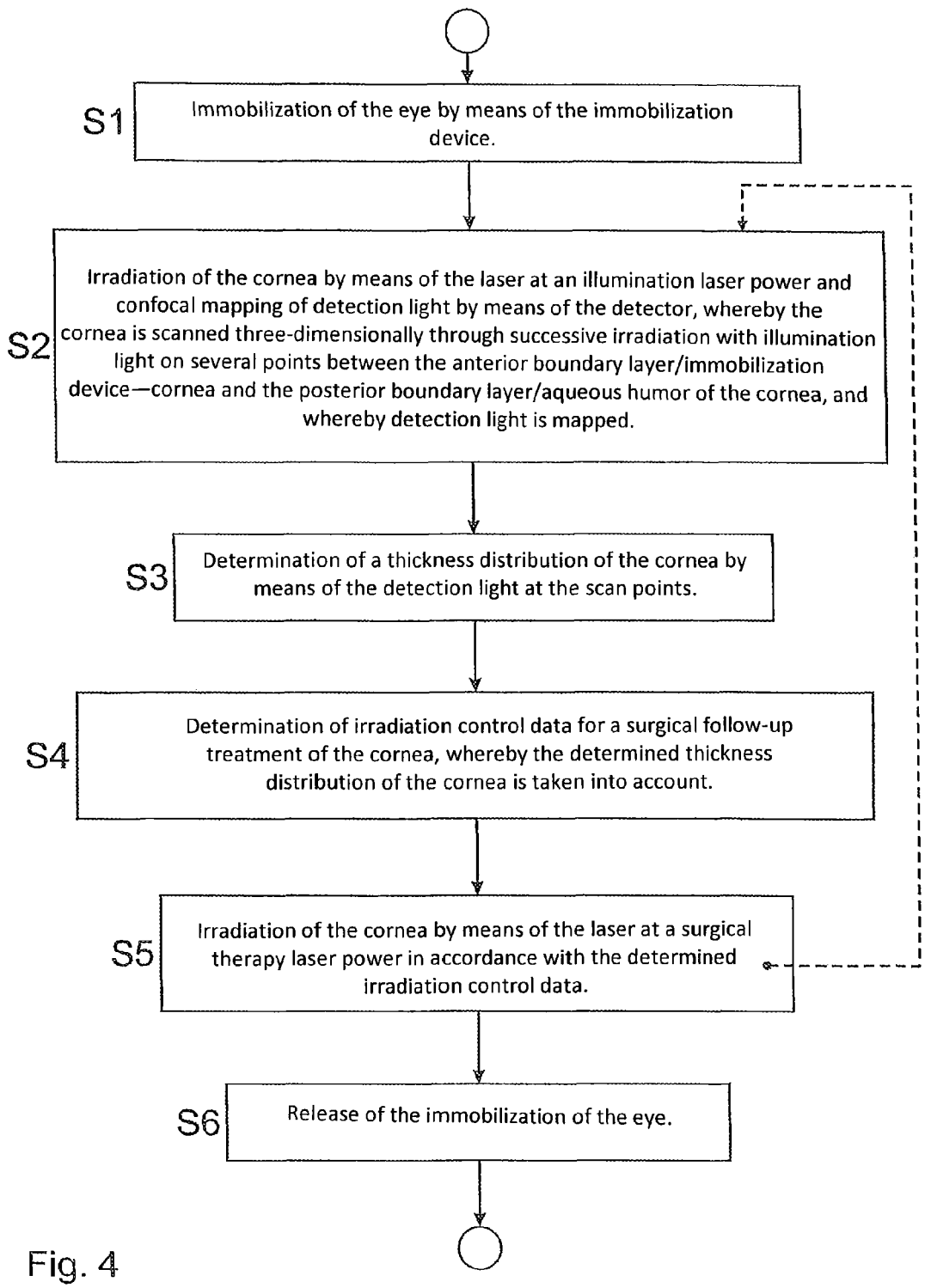
FIG. 4 is a flow diagram of an operating method.

The control unit 14 executes the operating method as shown in FIG. 4, whereby for a pure determination of position and/or form (without therapeutic treatment) of the posterior boundary layer 2.2 of the cornea 2 only the solidly outlined steps S1, S2, S3, and S6 are executed. For treatment, all steps are executed. Thereby, the same laser 4 is utilized not only for illumination during the confocal detection phase but also for the treatment of the cornea 2 during the immediately following treatment phase.

At first, the eye 3 of the patient is immobilized, for example, sucked towards a contact glass device by means of a vacuum (step S1). In addition, the head of the patient can also be immobilized. Through a suitable target, the eye position of the patient can be kept as constant as possible. Thereby, an adjustable compensation of the angle between geometric and optical axis of the eye 3 is possible.

The illumination light at illumination laser power is guided across the cornea 2 along one or several adjustable, three-dimensional scan curves or scan structures, and detection light is mapped (step S2). Thereby, the pulse frequency, in dependence of the speed of the scan movement, is adjusted in such a way that a lower pulse frequency results from a slow scan movement than from a fast scan movement. The backscattered detection light is assigned sectionally or pointwise to individual points P of the scan curve. With a consistent scan curve, consecutive scan points differ with regard to all spatial coordinates. From the detected signal values, respective dark-field values are advantageously subtracted, which are determined in a separate calibration phase.

From the intensities assigned to the scan points P, the posterior boundary layer 2.2 is identified and its form and position reconstructed (step S3) in order to determine a thickness distribution of the cornea 2. Thereto, for example, scan points, the intensity of which exceeds an intensity threshold, which is predetermined or specified by the surgeon, are determined as sampling points of the boundary layer 2.2. With an adjustment calculation, e.g., a model of the boundary layer 2.2 is adjusted to the three-dimensional coordinates of the determined sampling points in order to make available all coordinates of the posterior boundary layer 2.2 as a basis for the surgical treatment. Said information is used to adjust the incisions to be performed, e.g., predefined by the surgeon beforehand, to the actual individual condition of the cornea 2 before the irradiation control data are determined (step S4).

The irradiation control data comprise, e.g., control signals for the axes of the scanner unit 7 and/or the internal z-focusing, and for the laser beam source 4 and the power modulator 16.

Immediately thereafter, by means of the irradiation control data, the surgical treatment is executed at therapy laser power (step S5). Advantageously, pulse energies from 10 nJ to 3 µJ, particularly 50 nJ to 1 µJ are utilized. Thereby, for example, one or several series of photodisruptions are produced through the laser radiation at a pulse frequency from 100 kHz to 10 MHz and with a pulse length of less than 1 ps, particularly from 100 fs to 800 fs. Lastly, the immobilization of the eye 3 is released (step S6).

Due to the identical beam path for analysis and treatment, the system 1 is self-calibrating. Since the irradiation control data are determined by means of the information about form and/or position of the posterior boundary layer 2.2, obtained with the identical beam path, the treatment always allows for great accuracy.

Figure 5:
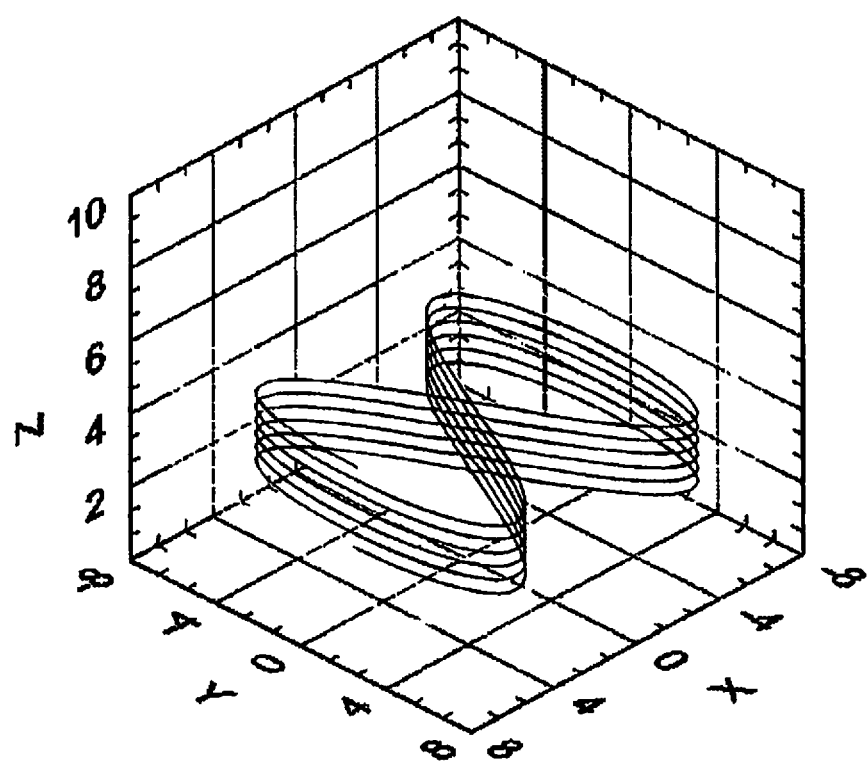
FIG. 5 depicts a space curve for the scanning of the cornea.

Through the use of adjusted scan curves (scan patterns), for example, in the form of Lissajous figures, the combined procedure can also be executed in a short period of time, for example, within a maximum of 30 seconds, which reduces inaccuracies due to movement and leads to better acceptance by the patient. FIG. 5 shows an exemplary scan curve in the form of spatially offset FIGS. 8, which can be realized as a Lissajous figure by means of the scanner unit 6.

Other exemplary forms of scanning and/or rastering can be (not depicted): two crossed rectangles in space; two cylindrical surfaces; a cylindrical body with a profile in the form of a FIG. 8 or 4; several scans along one-dimensional lines. It is also possible to raster the volume of a cylinder or a cube. The volumes and/or surfaces can be scanned continuously or only partially, i.e., with gaps between the individual scan points. As a result, greater distances can occur between individual lines.

For example, the invention in accordance with its first aspect can be used in all types of laser-supported cornea surgery, e.g., LASIK, in order to determine the actual (residual) thickness distribution of the cornea 2, for example, in treatment condition prior to or during surgery, particularly in applanated condition. Said thickness distribution can particularly be used to define and monitor safety distances from the boundary layers 2.1, 2.2.

In an ophthalmological laser system 1 in accordance with FIG. 3, the invention can also be realized according to its second aspect. Thereby, the control unit 14 can, after the above described first irradiation cycle and before the release of the immobilization device, activate the laser 4 with the attenuator 15, tilted into the illumination beam path B, for the illumination of the cornea 2 and produce a two-dimensional image of the cornea 2 by the detector 12. For example, with a still active immobilization of the eye 3, it can identify and localize OBL fields by means of digital image processing. Compared to the surroundings, the OBL fields are characterized through a detection signal with altered intensity and are easily localized, e.g., through a gray-scale value discriminator. Alternatively to the separate image acquisition, the control unit 14 can already map the two-dimensional image during the first irradiation cycle, whereby the illumination through the treatment light at surgical therapy laser power is utilized for the image acquisition. Thereto, the attenuator 15 is not required. Such embodiment has the advantage of not requiring additional time for an image acquisition. In a further embodiment (not depicted), the detection can be executed by means of a 2D camera or by means of an optical coherence tomography (OCT).

If the identified OBL field lies outside the accessible treatment diameter or if it is too small to have significant impact on the detachment behavior, the control unit 14, e.g., will not take it into consideration. If a significant OBL field is detected by the control unit 14, it is possible to execute a second complete laser incision, i.e., a repeated irradiation with the use of all previously utilized irradiation control data.

Alternatively, the repeated laser incision is only repeated in the area(s) affected by the OBL and is therefore a partial second laser incision.

Figure 6:
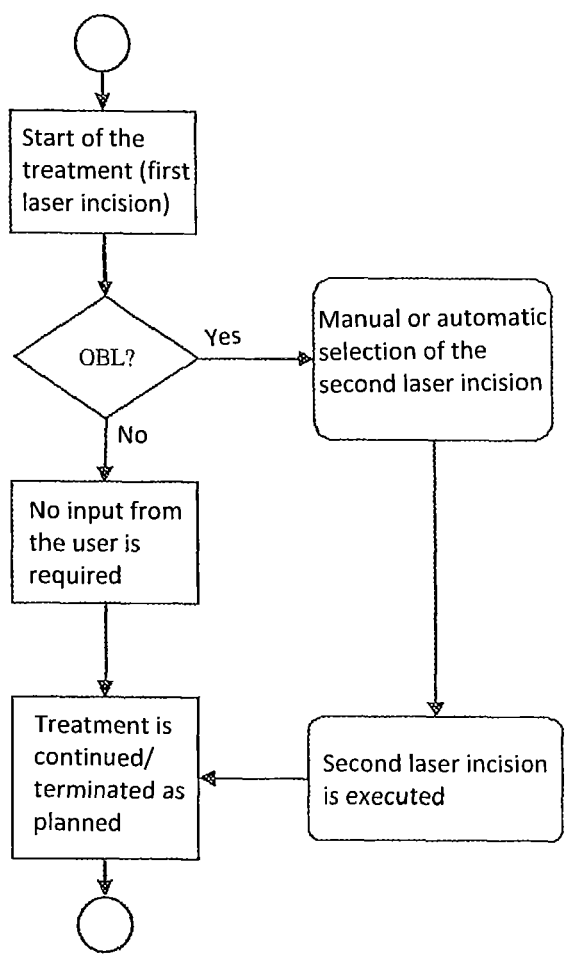
FIG. 6 depicts an example process in the form of a flow chart.
Figure 7:
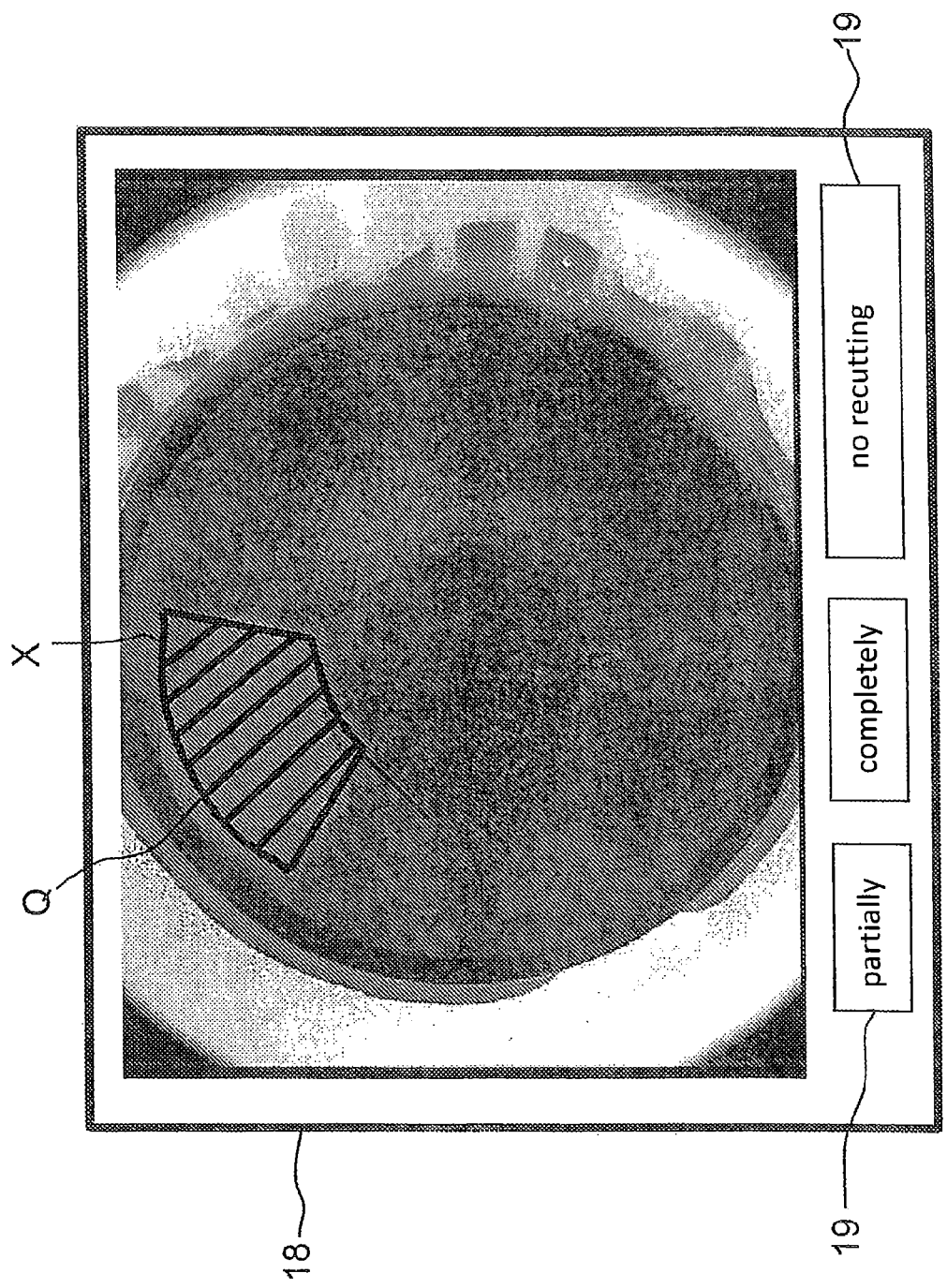
FIG. 7 is an image display depicting an image of a first time irradiated cornea with an area Q with OBL and an example area X for an automatically suggested recut.

The second laser incision can either be executed fully automated subsequent to the first laser incision or the user can be prompted to confirm said second laser incision. Said confirmation can take place on an image display in combination with the visualization of the automatically detected OBL fields and correspondingly planned laser incision zones. FIG. 6 shows an exemplary process in the form of a flow chart. In FIG. 7, an image display 18 with the image of a first-time irradiated cornea 2 with an area Q with OBL is indicated. Also indicated is an exemplary area X for an automatically suggested recut. By means of push buttons 19, which are implemented in software, the user can, e.g., choose between "partially" (partial laser incision of the OBL area), "completely" (a complete second laser incision in case of an insufficient automatic detection), and "no recutting" (the device does not execute a second laser incision and continues with the normal process, typically the release of the immobilization of the eye 3).

The described automation of the OBL detection via suitable detection methods is not necessarily required but adds additional convenience for the operator and can significantly reduce the additional radiation exposure through the option of the partial laser incision.

Further possible realizations:
a) Manual repetition of an identical laser incision
   The user monitors the course of treatment through a suitable observation device (screen, operating microscope, etc.). As a rule, the OBL fields occur immediately at the beginning of the treatment. If the user observes incidences of OBL fields, he/she can meanwhile trigger the automatic repetition of the laser incision through an appropriate input option at the laser system 1, particularly on the control unit 14.
b) Manual repetition of a non-identical laser incision
   After manual selection of the second laser incision (recut), said incision can differ from the first incision with regard to its parameters. Particularly, the energy, the spot and track distance as well as the scan direction can be varied in order to achieve a better treatment outcome.
c) Manual localization of the OBL fields with selective repetition of the laser incision
   During or shortly after the treatment, the user can, through an appropriate input option (pointer, touch on the camera image of the observation device) manually mark those areas in which the laser incision is subsequently repeated automatically.

LEGEND

1 Ophthalmological laser system
2 Cornea
2.1 Anterior boundary layer
2.2 Posterior boundary layer
3 Eye
4 Laser
5 Beam splitter
6 Scan optics
7 Scanner unit
8 Focusing optics
9 Optical phase retardation system
10 Deflection mirror
11 Confocal aperture diaphragm
12 Detector
13 Amplifier
14 Control unit
15 Attenuator
16 Modulator
17 Immobilization device
18 Image display
19 Push button
B Illumination beam path
D Detection beam path
P Scan point
L Planned lamella
Q Area with OBL
X Suggested area for repeated irradiation

The invention claimed is:

1. An ophthalmological laser system, comprising:
a laser, radiation of which is focusable in an examination region via an illumination beam path;
a scanner unit;
an immobilization device configured to immobilize an eye positioned in the examination region;
a detector that maps detection light from the examination region; and
a control unit configured to cause the following steps to be executed:
determining of irradiation control data for a laser surgical treatment;
activating of the immobilization device;
irradiating a cornea by the laser at a surgical therapy laser power in accordance with the determined irradiation control data at a first location and a first depth with a first irradiation;
illuminating the cornea;
identifying an area of the cornea, which contains opaque bubbles, by analysis of the detection light mapped by the detector;
repeating irradiation of at least the identified area of the cornea at the same first location and the same first depth by the laser at the surgical therapy laser power with at least one repeated irradiation; and
deactivation of the immobilization device;
wherein the immobilization device remains permanently activated between the first irradiation and a last of the at least one repeated irradiation.

2. The ophthalmological laser system, according to claim 1, wherein the control unit is further operable to cause the repeated irradiation in accordance with the determined irradiation control data or in accordance with a subset thereof.

3. An operating method for an ophthalmological laser system, the laser of which is switchable between an illumination laser power and a therapy laser power, and the laser light of which is focusable variably three-dimensionally in a cornea, comprising:
determining irradiation control data for a laser surgical treatment;
activating an immobilization device;
irradiating the cornea by the laser at a surgical therapy laser power in accordance with the determined irradiation control data at a first location and a first depth with a first irradiation;
identifying an area of the cornea which contains opaque bubbles, by analysis of images of the cornea;
repeating irradiation of at least the identified area of the cornea at the same first location and the same first depth by the laser at the surgical therapy laser power with at least one repeated irradiation; and
deactivating the immobilization device, wherein the immobilization device remains permanently activated between the first irradiation and a last of the at least one repeated irradiation.

4. The method, according to claim 3, further comprising storing the irradiation control data utilized for the repeated irradiation of the cornea in a treatment database; and utilizing the stored irradiation control data for the optimization of the irradiation control data.

5. A method of execution of a keratoplasty on a cornea of an eye, comprising:
immobilizing the eye by an immobilization device;
irradiating the cornea by a laser at a surgical therapy laser power at a first location and a first depth with a first irradiation;
identifying, after the irradiation of the cornea, an area of the cornea which contains opaque bubbles;
again irradiating at least the identified area of the cornea at the same first location and the same first depth by the laser at the surgical therapy laser power; and
releasing the immobilization device at the end of the irradiation.

6. The method, according to claim 5, further comprising executing the repeated irradiation in accordance with identical irradiation control data in the same manner as the first irradiation or in accordance with a subset thereof.

7. The method, according to claim 5, further comprising storing the irradiation control data utilized for the repeated irradiation of the cornea in a treatment database; and utilizing the stored irradiation control data for the optimization of the irradiation control data.

8. A non-transitory computer readable data medium including instructions to cause a computer to execute a method, comprising:
determining irradiation control data for a laser surgical treatment;
activating an immobilization device;
irradiating the cornea by a laser at a surgical therapy laser power in accordance with the determined irradiation control data at a first location and a first depth with a first irradiation;
identifying an area of the cornea which contains opaque bubbles, by analysis of images of the cornea;
repeating irradiation of at least the identified area of the cornea at the same first location and the same first depth with at least one repeated irradiation by the laser at the surgical therapy laser power; and
deactivating the immobilization device,
wherein the immobilization device remains permanently activated between the first irradiation and the last of the at least one repeated irradiation.

9. A non-transitory computer readable data medium including instructions to cause a computer to execute a method of execution of a keratoplasty on a cornea of an eye, comprising:

immobilizing the eye by an immobilization device;

irradiating the cornea by a laser at a surgical therapy laser power at a first location and a first depth with a first irradiation;

identifying, after the irradiation of the cornea, an area of the cornea which contains opaque bubbles;

prior to releasing of the immobilization, again irradiating at least the identified area of the cornea by the laser at the same first location and the same first depth at the surgical therapy laser power; and releasing the immobilization device at the end of the irradiation.

\* \* \* \* \*

UNITED STATES PATENT AND TRADEMARK OFFICE
CERTIFICATE OF CORRECTION

| | | |
|---|---|---|
| PATENT NO. | : 8,740,889 B2 | Page 1 of 1 |
| APPLICATION NO. | : 13/139994 | |
| DATED | : June 3, 2014 | |
| INVENTOR(S) | : Wilfried Bissmann et al. | |

It is certified that error appears in the above-identified patent and that said Letters Patent is hereby corrected as shown below:

In the Specification

Col. 6, line 56, delete "FIG. 8" and insert --figure 8--

Col. 13, line 35, delete "FIGS. 8" and insert --figures 8--

Col. 13, line 40, delete "FIG 8 or 4" and insert --figure 8 or 4--

Signed and Sealed this
Second Day of September, 2014

Michelle K. Lee
*Deputy Director of the United States Patent and Trademark Office*